United States Patent [19]
Willenbrock et al.

[11] 4,196,624
[45] Apr. 8, 1980

[54] PROBE ASSEMBLY

[75] Inventors: Helmut Willenbrock, Achim; Friedrich Schittek, Bremen, both of Fed. Rep. of Germany

[73] Assignee: Gustav F. Gerdts KG, Bremen, Fed. Rep. of Germany

[21] Appl. No.: 885,131

[22] Filed: Mar. 9, 1978

[30] Foreign Application Priority Data

Mar. 15, 1977 [DE] Fed. Rep. of Germany ....... 2711112

[51] Int. Cl.$^2$ ............................................. G01F 23/00
[52] U.S. Cl. ............................. 73/304 R; 174/15 BH
[58] Field of Search .................... 174/15 BH, 16 BH; 73/343 B, 343 R, 304 R, 304 C, 432 R, 86, 421.5 A, 359; 428/920; 106/75; 277/22

[56] References Cited

U.S. PATENT DOCUMENTS

| | | | |
|---|---|---|---|
| 1,379,897 | 5/1921 | Bradley | 174/15 BH |
| 2,652,725 | 9/1953 | Lamb | 73/343 R |
| 2,969,412 | 1/1961 | Frank | 277/22 X |
| 3,250,125 | 5/1966 | Bonn | 73/359 X |

*Primary Examiner*—Jerry W. Myracle
*Attorney, Agent, or Firm*—Allison C. Collard; Thomas M. Galgano

[57] ABSTRACT

A probe assembly is provided which includes a housing, at least one sensing element extending through a passageway in a wall of the housing and a sealing packing element mounted in the passageway for effecting a pressure-tight seal between the sensing element and passageway. The housing has a generally pipe-shaped neck portion, one end of which has disposed thereacross the housing wall through which the passageway extends, and the sensing element is at least partially disposed in the neck portion in a direction generally parallel to the longitudinal axis of the neck portion. The neck portion is filled with a heat-resistant, porous filler material, which prevents damage to the sealing packing element.

4 Claims, 1 Drawing Figure

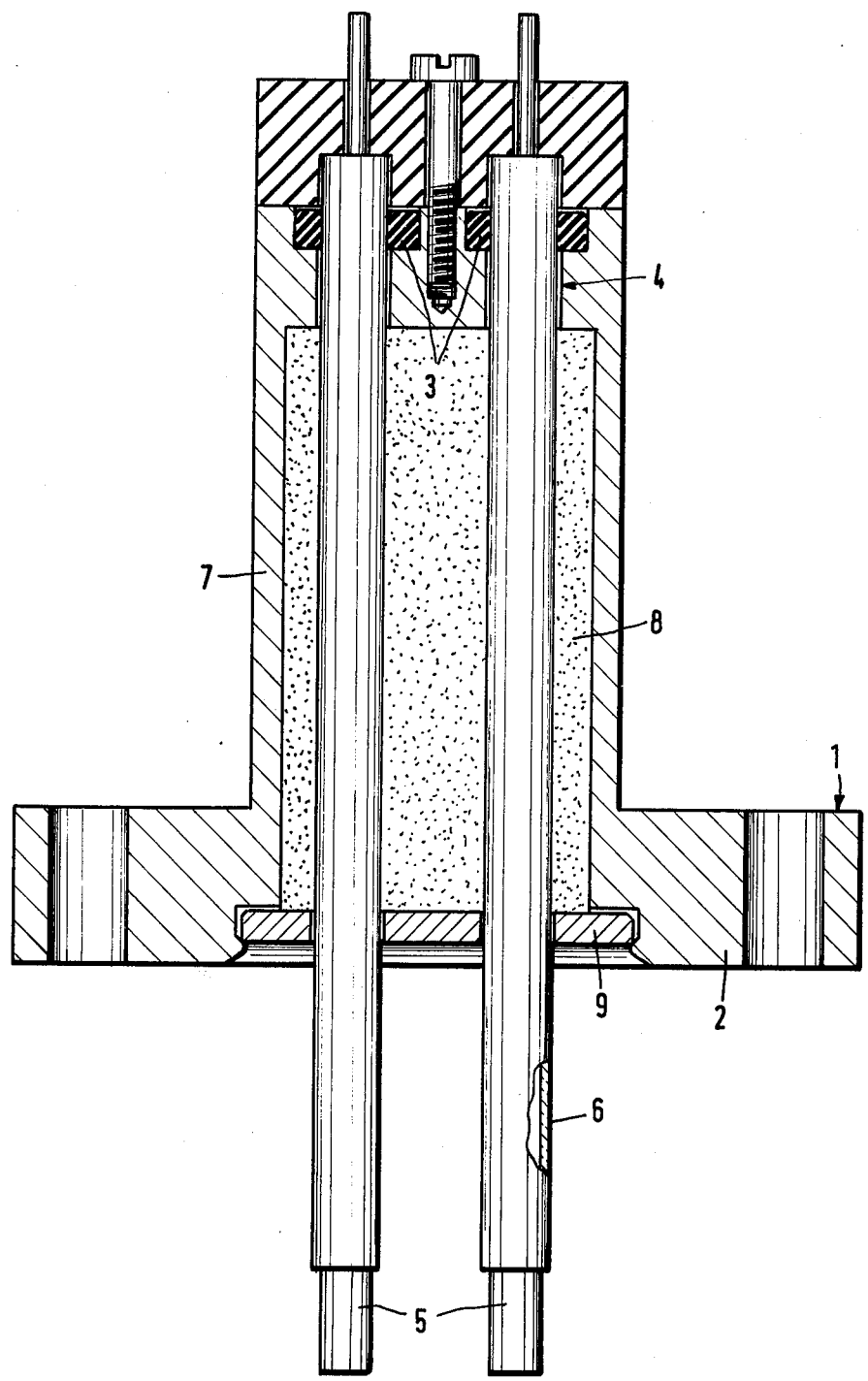

PROBE ASSEMBLY

The present invention relates to a probe assembly. More particularly, it relates to a probe assembly of the type which includes a housing, at least one sensing element extending through a passageway in the wall of the housing and a sealing packing element mounted in the passageway for effecting a pressure-tight seal between the sensing element and the passageway. The probe assembly is particularly useful for controlling the level of electrically-conductive liquids or for controlling the conductivity of liquids, for example, by using electrodes as the sensing elements, or for measuring temperature conditions, by using thermal elements as the sensing elements.

The sealing materials which are suitable for effecting a pressure-tight seal of the wall passageway for the sensing elements, for example, elastic sealing rings and packings, are extremely restricted since the permissible operational temperatures for the available sealing materials are so low that they do not meet the requirements necessary for steam boilers operating under high pressures and high operating temperatures.

It is, therefore, an object of this invention to provide an improved probe assembly of the above-mentioned type which can be used in steam devices having a high steam temperature and can, therefore, be used in devices operating under high pressures.

This object is attained in accordance with the present invention by the provision of a probe assembly of the aforementioned type which is characterized by the employment of a housing having a pipe-shaped neck which is filled with a heat resistant porous filler material. One end of the neck has a housing wall extending thereacross through with the passageway for the sensing element extends. The sensing element is at least partially disposed in the neck portion in a direction generally parallel to the longitudinal axis of the neck portion.

The inventive neck which is filled with porous filler material is coupled between the steam chamber of the steam device to be controlled and the temperature sensitive wall passageway and sealing elements of the probe assembly. The steam which penetrates into the pores of the filler material condenses due to the heat emission to the outside atmosphere. The cooler condensate is retained in the pores of the filler material and presents the hot steam, which is damaging to the sealing material, from reaching the sealing material at the wall passageway.

Preferably, the opposite end of the neck remote from the wall passageway is provided with a removable and exchangeable cover for charging the filler material into the neck. The sensing element extends through the cover, the latter of which permits the use of differently-shaped sensing elements, as well as the employment and different arrangement of a plurality of sensing elements.

Mostly advantageously, the filler material is a bulk material, such as sand, since it is very suitable for purposes intended and economical as well.

Other objects and features of the present invention will become apparent from the following detailed description when taken in connection with the accompanying drawing which discloses a single embodiment of the invention. It is to be understood that the drawing is designed for the purpose of illustration only, and is not intended as a definition of the limits and scope of the invention disclosed.

In the drawing, a sectional view, in part elevation, of a novel probe assembly embodying the present invention for monitoring the level of an electrically-conductive liquid is illustrated.

Referring now in detail to the drawing, a housing 1 is provided at its lower end with a flange 2 for connection to a steam device or apparatus. Housing 1 is provided at its upper end with two wall passageways 4, in each of which is mounted a sealing packing 3. An electrode 5 which acts as a sensing element, extends through each sealing packing 3 and passageway 4. Electrodes 5 are each provided with an insulation jacket 6 which surrounds the electrode up to a certain desired length.

A pipe-like neck 7 of housing 1 extends between flange 2 and wall passageways 4. Electrodes 5 extend longitudinally through neck 7 and protrude outwardly therefrom. Neck 7 is filled with a porous filler material 8; in this case, washed sand. At the flange side, that is, at the end of neck 7 farthest away from wall passageways 4, a cover 9 is provided in the shape of a disc through which electrodes 5 extend with suitable radial clearance. Cover 9 is provided so as to prevent a leaking of sand from neck 7.

During operation, the steam penetrates through the annular slot between electrodes 5 and cover 9 and into filler material 8. Due to the heat emission of neck 7 to the outside atmosphere, a condensation of the penetrated steam occurs. The condensate which is colder with respect to the steam collects in the pores of the filler material (i.e., between the sand grains) due to the capillary action in the filler material. This prevents the approach of the hot steam to the temperature-sensitive sealing packings 3 of wall passageways 4. The condensate temperature which prevails at the wall passageways 4 can be adjusted by changing the dimensions of the length of neck 7, so that the condensate temperature will be at a value acceptable for the sealing packings 3 (i.e., the temperature of the condensate adjacent the wall passages 4, which is influenced by the length of neck 7, will be adjusted to a value which is within the permissible operating temperatures of the sealing packings 3.

Therefore, the probe assembly may be used in steaming plants or devices wherein the steam temperature is above the permissible operating temperature of sealing packings 3.

In view of the adaptability of filler material 8, a great variety of application possibilities exist concerning size, shape and number of the measuring elements employed without changing neck 7.

While only a single embodiment of the present invention was shown and described, it will be obvious to those persons of ordinary skill in the art that many changes and modifications may be made thereunto without departing from the spirit and scope of the invention.

What is claimed is:

1. In a probe assembly which includes a housing, at least one sensing element extending through a passageway in a wall of the housing and a sealing packing element mounted in a passageway for effecting a pressure-tight seal between the sensing element and passageway, the improvement comprising:

said housing having a generally pipe-shaped neck portion having two ends, one end of which has disposed thereacross said housing wall through which said passageway extends, said sensing element being at least partially disposed in said neck portion in a direction generally parallel to the longitudinal axis of said neck portion, and said neck portion being filled with a heat-resistant, porous filler material, said filler material being a bulk material and the other end of said neck portion being provided with cover means, which prevents said bulk material from passing therethrough, but which permits said sensing element to pass therethrough and project outwardly from said neck portion.

2. The probe assembly according to claim 1, wherein said bulk material is sand.

3. In a probe assembly for directly monitoring a medium in a device, which assembly includes a housing, at least one sensing element extending through a passageway in a wall of the housing and a sealing packing element mounted in the passageway for effecting a pressure-tight seal between the sensing element and passageway, the improvement comprising:

said housing having a generally pipe-shaped neck portion having two opposite ends, one end of which has disposed thereacross said housing wall through which said passageway extends, and the other end of which is disposed for communication with the medium, said sensing element being at least partially disposed in said neck portion in a direction generally parallel to the longitudinal axis of said neck portion, and projecting outwardly from said other end of said neck portion being filled with a heat-resistant, porous filler material, which, in cooperation with said neck portion, serves to protect said sealing packing element from the prevailing operating temperature of the medium, by dissipating the heat thereof, said filler material being a bulk material and the other end of said neck portion being provided with cover means which prevents said bulk material from passing therethrough but which permits said sensing element to pass therethrough and project outwardly from said neck portion.

4. The probe assembly according to claim 3, wherein said bulk material is sand.

* * * * *

UNITED STATES PATENT AND TRADEMARK OFFICE
CERTIFICATE OF CORRECTION

PATENT NO. : 4,196,624

DATED : APRIL 8, 1980

INVENTOR(S) : HELMUT WILLENBROCK & FRIEDRICH SCHITTEK

It is certified that error appears in the above—identified patent and that said Letters Patent is hereby corrected as shown below:

Column 1, line 36, change "with" to --which--.
Claim 1, line 4, change "a" (first occurrence) to -- the --.

*Signed and Sealed this*

*Nineteenth* Day of *August 1980*

[SEAL]

Attest:

SIDNEY A. DIAMOND

*Attesting Officer*    *Commissioner of Patents and Trademarks*